US009996672B2

(12) United States Patent
Lo et al.

(10) Patent No.: US 9,996,672 B2
(45) Date of Patent: Jun. 12, 2018

(54) SYSTEMS AND METHODS OF TREATMENT USING INTERVENTION AND TASKING DETERMINATION

(71) Applicant: Corcept Therapeutics, Inc., Menlo Park, CA (US)

(72) Inventors: Steven Lo, Menlo Park, CA (US); David Penake, Menlo Park, CA (US); John Lyons, Menlo Park, CA (US); Kate Tully, Menlo Park, CA (US); Katherine Waidner, Menlo Park, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 803 days.

(21) Appl. No.: 14/493,125

(22) Filed: Sep. 22, 2014

(65) Prior Publication Data

US 2015/0088540 A1    Mar. 26, 2015

Related U.S. Application Data

(60) Provisional application No. 61/880,785, filed on Sep. 20, 2013.

(51) Int. Cl.
*G16H 50/20* (2018.01)
*G06F 19/00* (2018.01)
*A61B 5/00* (2006.01)

(52) U.S. Cl.
CPC ............ *G06F 19/345* (2013.01); *A61B 5/742* (2013.01); *G06F 19/328* (2013.01); *G16H 10/60* (2018.01);

(Continued)

(58) Field of Classification Search
CPC ......... A61B 5/00; A61B 5/742; A61B 5/7465; A61B 5/7405; A61B 5/4848;
(Continued)

(56) References Cited

U.S. PATENT DOCUMENTS 7,945,461 B2   5/2011   Sekura
7,959,568 B2   6/2011   Stahmann et al.
(Continued)

FOREIGN PATENT DOCUMENTS

WO   2010044683 A1   4/2010
WO   2011/054000 A1   5/2011

OTHER PUBLICATIONS

EP14846696.4, "Extended European Search Report", dated Feb. 15, 2017, 11 pages.
(Continued)

*Primary Examiner* — Linh Giang Le
(74) *Attorney, Agent, or Firm* — Kilpatrick Townsend & Stockton LLP

(57) ABSTRACT

Devices, systems, and methods for use in managing patient treatments utilizing pharmaceutical or therapeutic compounds. Methods include accessing one or more fields of information relating to any of a patient, physician and drug treatment and relating the one or more fields, or combination thereof, to a particular attribute or outcome. By analyzing the one or more fields of data in relation to the attribute or outcome, the system determines suitability of an intervention(s) and tasks the intervention(s) to one or more entities to facilitate the desired attribute or outcome. In certain aspects, the system facilitates identification of complex relationships and trends between seemingly unrelated fields of information and outputs information for use in an intervention or various other purposes according to the attribute or outcome desired by the user.

19 Claims, 12 Drawing Sheets

(52) U.S. Cl.
CPC ............ *G16H 50/20* (2018.01); *A61B 5/4833* (2013.01); *A61B 5/4848* (2013.01); *A61B 5/7405* (2013.01); *A61B 5/746* (2013.01); *A61B 5/7465* (2013.01)

(58) Field of Classification Search
CPC ...... A61B 5/4833; A61B 5/746; A61K 31/50; G06F 19/00; G06F 19/345; G06F 19/328; G06Q 10/00; G06Q 50/00; G16H 50/20; G16H 10/60
See application file for complete search history.

(56) References Cited

U.S. PATENT DOCUMENTS

| | | | |
|---|---|---|---|
| 8,666,926 | B1 | 3/2014 | Nease et al. |
| 2002/0143579 | A1 | 10/2002 | Docherty et al. |
| 2006/0089542 | A1 | 4/2006 | Sands |
| 2006/0271405 | A1 | 11/2006 | Cipolle et al. |
| 2008/0126130 | A1 | 5/2008 | Miller et al. |
| 2008/0306359 | A1* | 12/2008 | Zdeblick ............. A61B 5/0028 600/302 |
| 2009/0048868 | A1 | 2/2009 | Portnoy et al. |
| 2011/0105852 | A1* | 5/2011 | Morris .................. G06Q 10/10 600/300 |
| 2011/0137682 | A1* | 6/2011 | Hoffman ............... G06Q 50/22 705/3 |
| 2012/0201747 | A1* | 8/2012 | Altschul ................ A61K 31/00 424/1.11 |
| 2012/0271647 | A1 | 10/2012 | Betses et al. |
| 2012/0316897 | A1 | 12/2012 | Hanina et al. |
| 2013/0131030 | A1 | 5/2013 | Belanoff et al. |
| 2014/0039445 | A1 | 2/2014 | Austin et al. |

OTHER PUBLICATIONS

PCT/US2014/056830, "International Preliminary Report on Patentability", dated Mar. 31, 2016, 8 pages.
SG11201602174S, "Written Opinion", dated Feb. 27, 2017, 7 pages.
International Search Report and Written Opinion dated Jan. 13, 2015, from International Application No. PCT/US2014/056830 (10 pages).
CN201480063385.4, "Office Action", dated Jan. 10, 2018, 17 pages.

* cited by examiner

Fig. 6A

| | Dosing | | | | | |
|---|---|---|---|---|---|---|
| Physicians | March | April | May | June | July | |
| Smith | | 300 | 150 | 150 | 150 | |
| Johnson | 300 | 300 | | | | |
| Williams | 300 | 300 | 300 | | | |
| Jones | 300 | 300 | 300 | 300 | | |

*Fig. 6B*

| FILTERS | Patient ID | Patient Name | MD Last Name | Status | PA Required | PA TAT | Appeal Required | Appeal TAT | Starter | PAP | WORD | Enrollment Date | Titrated | Dose (mg/day) | Duration (Weeks) | Late Flag |
|---|---|---|---|---|---|---|---|---|---|---|---|---|---|---|---|---|
| >Enrollment Date | 123 | xxxxxxx | Smith | Shipped | | | | | | | | 1/1/2013 | x | 600 | 63 | x |
| >MD Last Name | 124 | xxxxxxx | Jones | Shipped | x | 11 | | | | | | 10/1/2012 | | 300 | 65 | |
| > | 125 | xxxxxxx | Adams | Shipped | | | | | | | | 8/1/2012 | | 300 | 64 | |
| | 126 | xxxxxxx | Smith | Discontinued | x | 7 | x | 5 | 5 | | | 12/1/2012 | | 300 | 0 | x |

*Fig. 6C*

SYSTEMS AND METHODS OF TREATMENT USING INTERVENTION AND TASKING DETERMINATION

CROSS-REFERENCES TO RELATED APPLICATIONS

This application claims the benefit of priority to U.S. Provisional Application No. 61/880,785, filed on Sep. 20, 2013, the entire contents of which are incorporated herein by reference.

BACKGROUND OF THE INVENTION

The present invention generally pertains to treatments utilizing administration of pharmaceutical or other therapeutic compounds.

While medical treatments utilizing administration of pharmaceutical or therapeutics are widespread, the effectiveness of a given treatment may vary widely from patient to patient. Even when the efficacy of a given treatment has a high degree of predictability in most patients, the success of treatment may still vary considerably based on the patient's compliance with the prescribed treatment as well as the ability of the physician to prescribe an appropriate treatment regimen for a given patient. These difficulties can become even more problematic when the effect of a treatment and associated pharmaceutical or therapeutic is less predictable, varying considerably between patients.

Given the complexities and challenges posed by conventional approaches to treatments utilizing administration of pharmaceuticals, there exists a need for methods of treatment that provide improved patient outcomes and patient compliance. There further exists a need to provide improved management and administration of such treatments.

BRIEF SUMMARY OF THE INVENTION

The present invention generally pertains to treatments utilizing administration of pharmaceutical or other therapeutic compounds. In particular, the invention pertains to methods of managing such treatments by identifying suitability of interventions and tasking an individual or entity with the intervention to improve patient compliance, treatment outcomes or other desired result.

BRIEF DESCRIPTION OF THE DRAWINGS

FIG. 6A illustrate an example user interface display in an embodiment of the system.

FIGS. 6B-6C illustrate example user reports provided by a system of an embodiment.

DETAILED DESCRIPTION OF THE INVENTION

The present invention generally provides methods and systems for use in patient treatments, particularly in patient treatments utilizing one or more drugs or therapeutic compounds. In certain aspects, the system provides methods of treatment that utilize a relational database or information system that accesses fields of information relating to a patient, physician, or treatment are and analyzes the fields of information to determine and/or identify relationships between one or more fields and a desired attribute or result. The desired attribute or result may include any of: improved patient compliance or treatment outcomes, physician compliance, adherence to a treatment regimen or associated updates or modification to a regimen or associated follow-up. Using the relationship, the system may identify a need for an intervention and task the intervention to one or more entities to facilitate the desired result.

In an example embodiment, the system provides a relational database system in which one or more fields of information relating to a patient, physician and drug treatment are accessed and analyzed to determine suitability of an intervention based on a relationship between any of the fields of information or combinations thereof, and a desired attribute or result, such as patient compliance, improved patient outcome or other concern. Using the fields of information and one or more algorithms, the system determines when an intervention is suitable, what type of intervention is needed, and tasks an appropriate entity (e.g. a physician, patient advocate, drug developer) to perform the intervention. For example, the system may determine from patient and physician data that a particular patient is unlikely to continue treatment or may likely experience a sub-optimal treatment result. A suitable intervention may include outreach to a patient or physician by a pharmacy or by the drug developer to provide an indication or communication to the physician or patient of information associated with the treatment regimens or information relating to the patient so as to improve patient compliance. The intervention may be tasked by various means, such as an electronic communication or an alert through e-mail or wireless device, to one or more entities suitable for performing the intervention. Thus, by identifying the suitability of an intervention, often before observable sub-optimal outcomes or attributes develop, and tasking an appropriate entity to perform the intervention, the system facilities the desired outcome or attribute, thereby improving patient outcomes or facilitating treatment or other related concern.

Figure 1:
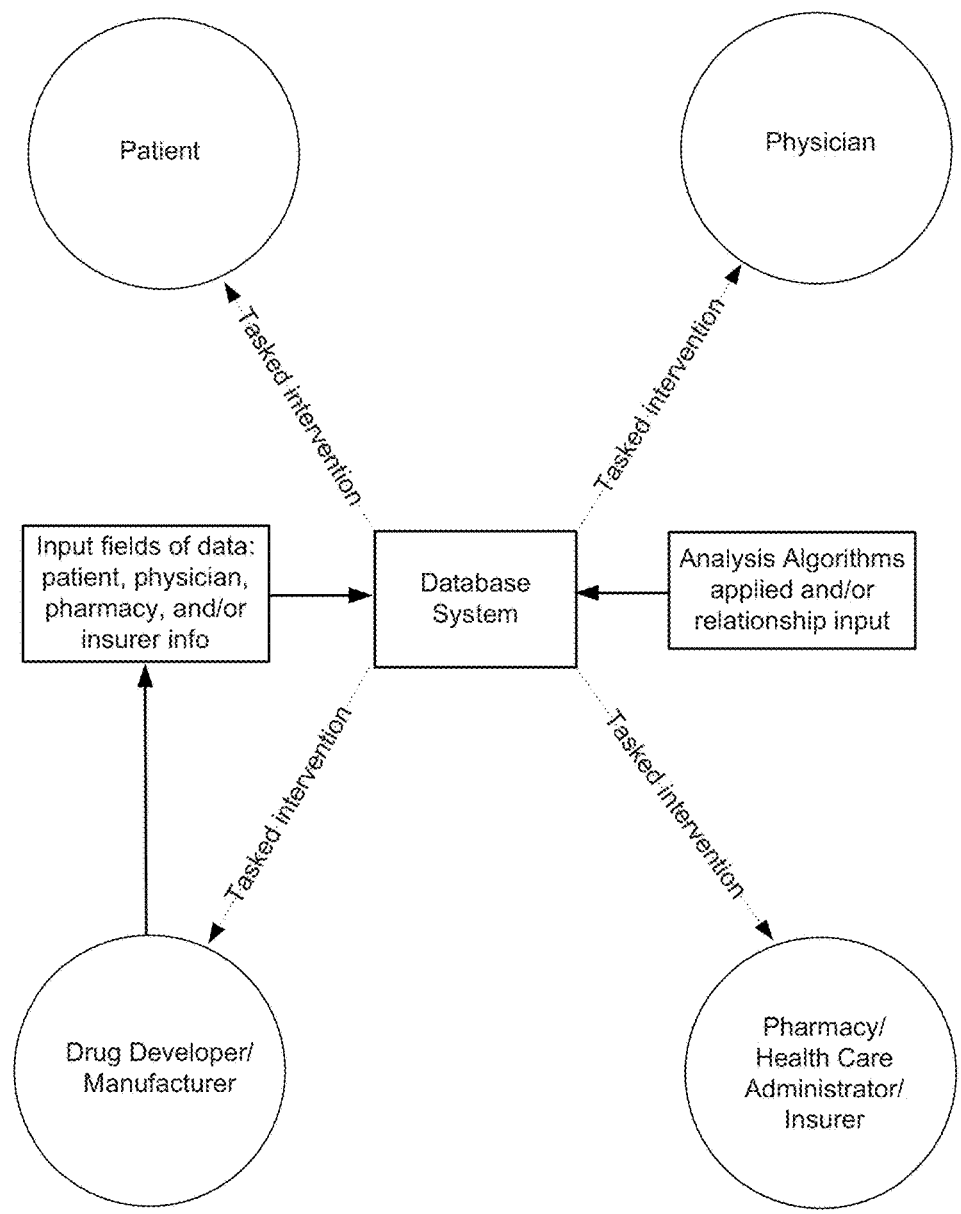
FIG. 1 illustrates a graphical system overview of example embodiment of the invention.

These aspects described above can be further understood by reference to FIG. 1, which illustrates a system in accordance with the present invention. This system includes a relational database system in which fields of information are related to one another. In certain aspects, the relationship information may access fields of information stored in different databases associated with multiple different entities such that all fields of information are not required to be stored on a single database. This allows for improved operation of the system by reducing storage requirements and streamlining analysis of accessed data. This also allows the relational database to analysis dynamic data since the information stored in the different existing information systems maintained by various different entities (e.g. hospital, physician, pharmacy, regulator). In another aspect, any or all of the fields of information may be stored within a readable memory within a system including the relational database. The fields of information may be stored on one or more databases and typically are input by one or more entities, for example by the drug developer, and the information is analyzed according to one or more algorithms or relationships stored in a processing unit of the system. The relationships or algorithms may be determined by the processing unit in a number of ways. The relational database system described herein may utilize a database, one or more inputs by a user and one or more user display interfaces for communication an intervention or task to a user. The system may utilize a processing unit having one or more processor, a server and may include a readable memory for storing information and/or algorithms associated therewith, which may include physical memory components or a cloud server.

In certain examples, the relationships or algorithms may be automatically determined by the system based on statistical analysis of the information, may be input by or more entities as they become known, such as determined through clinical studies, or may be automatically updated to the system from any number of sources accessed by the system In this example, the information and algorithms are input on a relational database system maintained by the drug developer, although it is appreciated that the information and algorithms input into the system can be received from various different entities or uploaded automatically from various different databases or information sources. Once the system relates the fields of information with one another and/or to a desired attribute or result (e.g. improved patient outcome, patient compliance, reduced shipping times or reimbursement processing times), a suitable intervention is identified and tasked to the appropriate entity. The system may determine one or more interventions based on the relationship of the information to the desired attribute/result and may task the one or more interventions to one or more entities. FIG. 1 illustrates the system tasking an intervention to each of the entities, although it is appreciated that, in many cases, a suitable intervention may be tasked to fewer than all entities or may include a particular sequence of interventions by one or more entities.

An important aspect of the system lies in the disparate data sets of information that are not accessible by any single individual or organization without such a database. The relational database has the ability to compare data fields from different incoming datasets (pharmacy data, patient advocate data, insurer information, etc.) and make an assessment about whether the data represent the same individual person. Once identified, the relational database can assign a unique identifier that connects all unique identifiers in the incoming datasets such that all future information is related to the unique individual. To provide an example of how this might be done, we may receive; shipment information that provides destination zip code and patient name from a pharmacy, patient name and city from the database that the Patient Advocate Program manages, the name of someone commenting about their disease on Facebook and patient name and prescription dose from the hub services organization. In each of these datasets, the individual will have different unique identifiers. It is only the constant comparison of data that may allow the database to identify that these are in-fact the same patient by relating specific identifiers (name, location, prescription quantity, ship quantity, etc.) Without a relational database that operates on a constantly refreshing basis, the ability to tie information together would be difficult and would inhibit the ability of the system to identify risks and generate actionable tasks.

Once a unique identifier is available for each patient, all data can provide a complete picture of what is happening and what interventions might be need to take place. For example, if a patient were identified as having a denial for coverage based on a new prescription, the database would have information to compare insurance. The database could compare this denial with patients that have the same diagnosis codes (from the pharmacy), same quantity for prescription (pharmacy), same health insurance plan (hub services provider) and identify potential reasons for the outcome. Upon comparing, the system might identify that the most likely reason for the denial is administrative error. In that case, it could task the hub services provider or local field person to speak with the office and have them review appeal documentation with the appropriate person in the practice or associated network of supporting personnel to remedy the error.

In another aspect, the system allows for analysis and identification of one or more fields of information in relation to a desired attribute or result. For example, the one or more fields of information may relate to a patient, physician, pharmacy, insurance, disease state, drug or therapeutic, drug shipments, various administrative programs or processes, or any combination thereof. The system accesses the fields of information in a relational database such that one or more fields of information, or combinations thereof, can be analyzed and a relationship between the information and a desired attribute or result can be identified and/or determined. Some or all of the fields of information may be stored on the database, or may remain stored on different databases, many of which are not accessible between or the types of information compatible with for comparison/analysis, outside of the system of the present invention.

Figure 2:
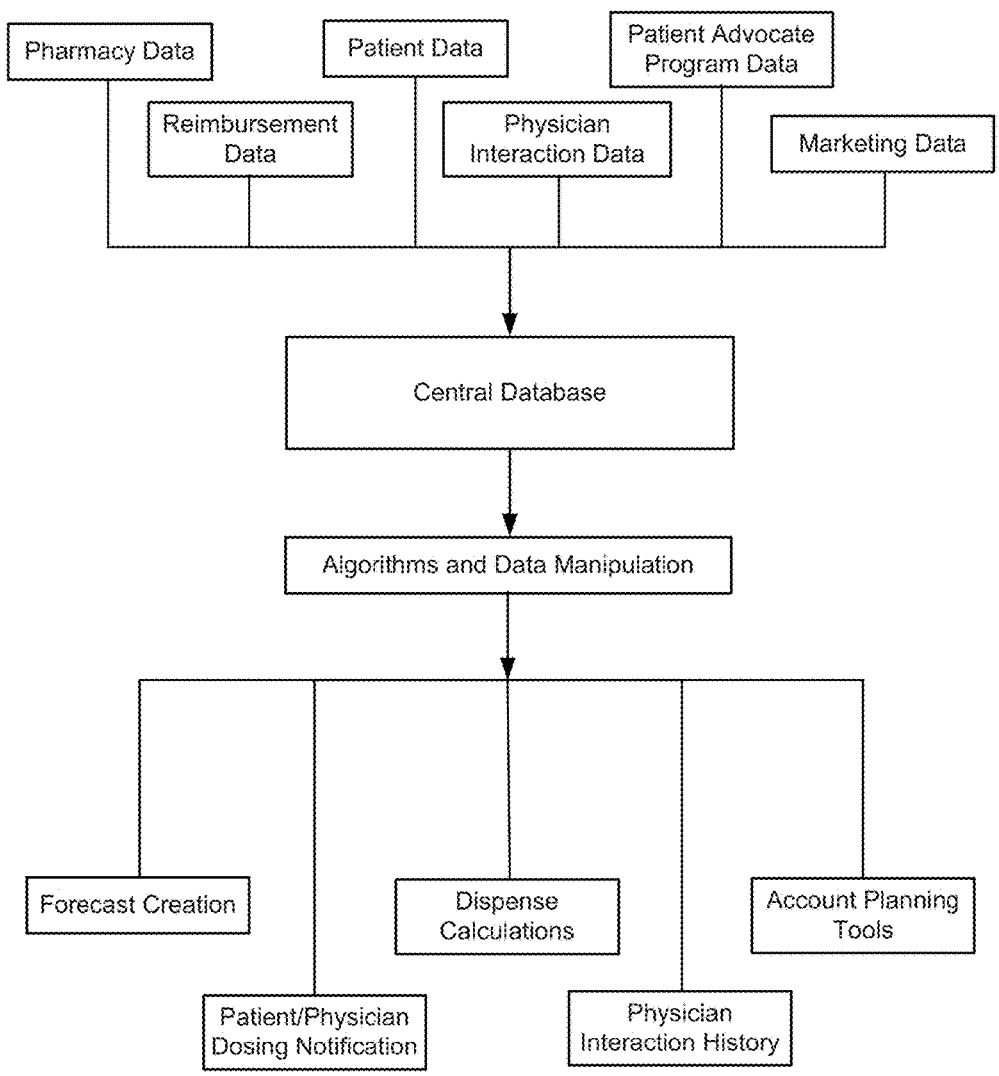
FIG. 2 illustrates an information flow diagram in an example embodiment, in accordance with methods of the invention.

The attribute or result of which a user may desire to determine the likelihood of based on the information may include any of a treatment outcome, patient compliance, or various attributes associated with treatments or various business or administrative concerns, such as shipping, accounting, and payment processes relating to the medication or therapeutic compound. In such embodiments, the system may provide an output of information that identifies the relationships or an output according to a custom report to be used for various other purposes, for example, forecast creation, budgeting, administration, or planning FIG. 2 illustrates various different types of information that may be input into a central database, in accordance with certain embodiments of the invention, as well various different outputs of information that may be provided by relating the fields of information to a desired attribute or result. In this example, the different fields of information include any of pharmacy data, patient data, patient advocate program data, reimbursement data, physician interaction data and marketing data, while the information output from analyzing and relating the various fields of information include any of forecast creation, dispense calculations, account planning tools, patient/physician dosing notification, dispense calculations, physician interaction history, and various account planning tools.

Figure 3:
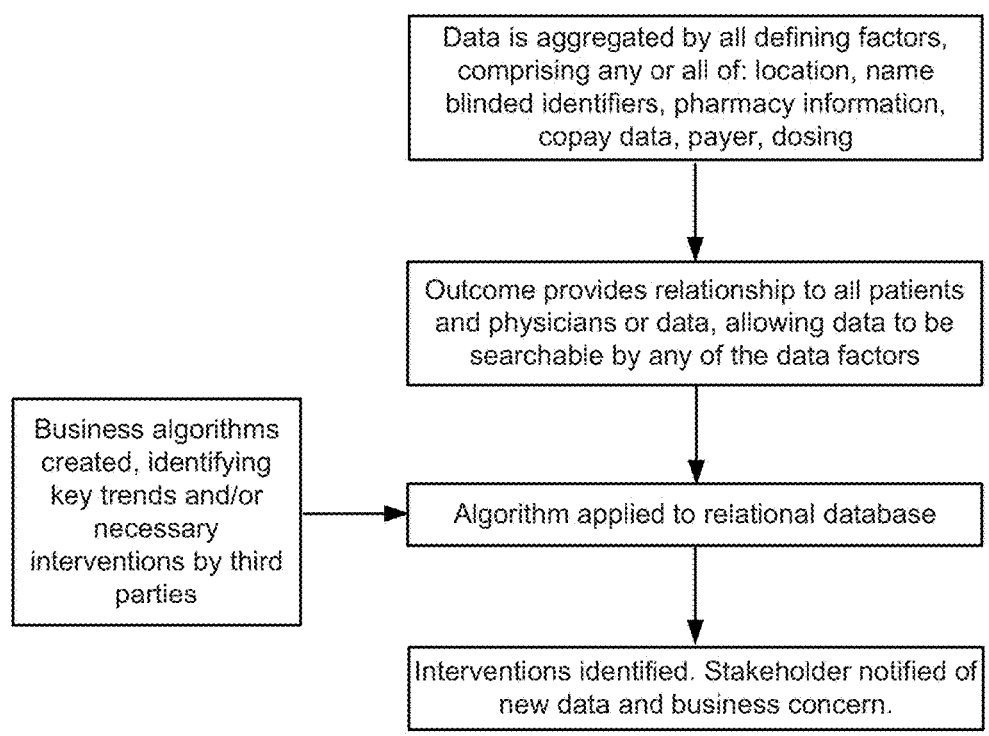
FIG. 3 illustrates an information flow diagram of data manipulation in an embodiment, in accordance with methods of the invention.

FIG. 3 illustrates a process flow chart within a relational database in certain embodiments of the system. The system obtains data as one or more fields of information and aggregates the information by various defining factors, for example: location, name, blinded identifiers, pharmacy information, copay data, payer, and dosing. The system relates the fields of information to one or more other fields of data such that the fields of information may be searchable on various levels by one or more data factors. For example, a first field of information, such as a patient identifier may be associated with at least a second field of information, such as the patient name, the treatment, the drug, the physician, the insurer, etc., thereby allowing the first field of information to be searchable by the one or more second fields of information. These fields of information, or various combinations thereof, may be associated with a desired attribute or result (e.g. improved patient compliance or treatment outcomes), such that analyzing the information on or more levels or analyzing various fields of information or combinations of fields using an algorithm of the system identifies suitability of an intervention (or alternatively a desired information output). The algorithm may include business algorithms created by a user of the system and input into the processing unit of the system or may be determined by the processing unit by applying an algorithm, such as a statistics analysis. The algorithms may relate to key trends, such as various business concerns, or may relate to an intervention by a third party, such as an alert to the drug developer to contact a physician or patient regarding treatment. Once the intervention is identified, the intervention is tasked to the appropriate entity, which may include notifying a stakeholder of the relevant information and of the potential concern.

Advantageously, by relating various types of seemingly unrelated data, the system allows for identification and analysis of various risk factors, even when the interactions between these factors may be unknown. For example, analyzing the fields of information, or various combinations thereof, in relation to a desired attribute or outcome, allows the system identify new relationships and associations between the fields of information, well before the interactions between the varies data factors are understood. Thus, the system allows for improved methods of treatment by analyzing current and/or real-time data from disparate sources to identify suitability of an intervention and tasking of the intervention to prevent undesirable outcomes. This approach may help identify and avoid undesirable trends in treatment in substantially less time than would otherwise be identified and addressed, if it all, in conventional practice.

I. System Overview

In an example embodiment of the invention, the methods utilize an information system storing or having access to a wide range of data associated with any or all of the patient, the physician, the pharmaceutical, and the drug protocol and allows integration of the data for use in analysis in managing the treatment methods (Part A). Analysis and use of the associated data utilizes a relationship database algorithm and a viewing function on a user interface (Part B). By use of relational algorithms, the system determines the suitability of an intervention (Part C) based on a relationship between one or fields of information of the data and a desired result or attribute. The relational algorithms may be input by a user or uploaded automatically into the system as such relationships are determined or become known. Once the suitability and need for an intervention is determined, the system tasks an individual or entity with the invention, which typically includes identifying and assigning an individual, entity, or computer to carry out the intervention (Part D). In some embodiments, the system monitors, tracks and confirms a status of the intervention to ensure that the intervention is carried out. Such systems may also record the response and outcome of the intervention, which may be fed back into the system to assist in determination of various aspects of subsequent interventions for that patient or various other patients.

To further illustrate the concepts described above, each is described in further detail below with respect to an example embodiment.

II. Part A: Data Structure and Integration

Pharmaceutical manufacturers have access to a wide variety of data including but not limited to pharmacy data, reimbursement patient data, data associated with patient specific interactions and programs, data associated with physician or nurse specific interactions and programs, marketing data, website interaction data, data from insurance companies, distributors and other $3^{rd}$ party service providers. In certain embodiments of the invention, the fields information from the disparate sources accessed and information associated with the fields of information are stored in a database in raw form that relates to the relationship of the data element. In one aspect, the disparate sources are external to the system and/or maintained by separate entities such that the information stored thereon is largely unrelated outside of the present system using the relational database. Data that has been provided from a pharmacy may include a blinded patient identifier along with information about location of the delivery, delivery transit time, the number of tablets, vials or other measurement of product included, date of delivery, remaining refills, and many other types of data elements. In one aspect, the patient identifier is blinded so that any other information associate with the patient and his/her treatment can be analyzed by the system and accessed by one or more entities external to the pharmacy and/or medical facility without comprising the patient's right to privacy. In certain aspects, the system may even communication a notification within a tasked intervention to a patient or a medical facility by use of the blinded unique identifier. Other types of data stored or accessed by the system may include data input through a website, symptom reporting data, website tracking data (IP address, web traffic data) or various other types of information. This data may be housed in a central database relating to the blinded patient identification code or the system may be configured to automatically access the data while stored on disparate sources and relate the data using one or more identifiers associated with the one or more fields of information.

Alternatively, the data may be stored over multiple databases and made accessible to a processor of the system such that data can be automatically accessed and analyzed by a processor of the system. Each of the data elements housed in the central database may be stored with a unique identifier that is largely unrelated to the identifiers associated with data from other sources mentioned above. For example, while some of the data noted above may be obtained by various entities (e.g. pharmacy, delivery service, physician) in conventional systems, such data is generally stored on disparate systems and associated with various identifies unrelated to the particular patient or treatment. The relational database receives information from each of the input databases on a daily basis and provides the ability to alter datasets that are sourced in the relational database in real-time. Thus, the invention may utilize this data, either input by the patient, physician, pharmaceutical manufacturer or third party or obtained through other means, by associating each data with the patient and/or treatment.

III. Part B: Relational Database

Once the data described above is stored on a central database or made available to a processing unit of the system, the system identifies and/or determines relationships between the data for various purposes (e.g. patient treatment, business analysis, etc.) using one or more identifiers associated with the data. Utilizing specific data element requirements and/or algorithms that identify relationships between the different data elements can transform a previously unrelated set of data and content from disparate sources to become a fully related set of data and content readily accessible to one or more entities. These specific element requirements (e.g. ranges of data values, thresholds, and maximum or minimum values) and algorithms (e.g. relationships between multiple data values, data trends over time, weighting of data) may be input into the system by a third party or may be determined by the system based on an association of the data relationships and a desired outcome (e.g. patient, treatment or business).

An example of a relationship between data elements that could be utilized in this case would be a combination of the number of days between when a patient receives shipment, the number of outreach attempts to contact the patient in which the person that conducted the outreach was unable to reach the patient (left a voicemail rather than speaking over the phone for example), the dose of the patient and how many refills are left on the prescription. This type of patient may trend themselves out of a population of patients that are likely to achieve a successful clinical result and are therefore likely to become non-compliant. When this is identified, the system could highlight this patient as high risk and task the Patient Advocate Program to contact the patient more regularly and pre-schedule the activities or it may recommend that a field representative speak with the physician about the optimal method of managing patients to ensure a proper clinical result. The system may, however, take those same data elements and apply two more pieces of information (prescribing physician and diagnosis codes) and be able to identify that the patient has more mild disease and is being treated in a similar manner to all other patients that the physician has prescribed the medication to. In this instance, it may weight more heavily on these data regarding disease severity and physician behavior and only suggest that the pharmacist reachout and offer another consultation as the risk for discontinuation or poor efficacy may be less likely when looking at patient specific information alone.

Applying these techniques allows the system to access data elements relate the elements to one another and output relationships between elements or analysis to a user or to automatically perform various functions in response to a determine relationship. With access to this system, a user has the opportunity to view data and unique reports output by the system, thereby allowing for ad-hoc analysis of the patient treatment or an associated administrative process. As an example, by identifying a shipping date for a prescription refill, the system can identify the amount of copay (relate to copay transaction date), physician name (relating to patient location or other reimbursement service providers), payer name and insurance information (relating to copay transaction information), and a most recent interaction between the company and the physician (relating to physician information) among many other possible combinations of relationships. An example custom report is shown in FIG. 6C.

IV. Part C: Data Analysis/Algorithms

In certain embodiments, the system applies data requirements and/or relational algorithms to the data information stored or access by the system to identify the need or suitability of an intervention. These data requirement and/or relational algorithms may be input into the system by any of the entities described herein or may be determined by the system itself based on data associated with results and outcomes of past interventions relating to the same or similar data. In one example, the system analyzes data relating to dosing, on a physician level, in particular the dosing prescribed by a particular physician to their patients. Data relating to these aspects are illustrated in the sample user report shown in FIGS. 6B. Studies have shown that treatment often vary according to the physician administering the treatment, such that associating a patient and treatment with their physician, can identify a need for an intervention with the physician rather than the patient to assess or modify the manner in which the physician is prescribing or administering the treatment. If the patient dosing does not progress with either: prior dosing for the physician that is deemed acceptable given clinical data supporting efficacy or dosing falls behind our clinical data when there is minimal prior physician data, the system identifies these physicians as being at risk to proper treatment. Whether treatment of a patient results in favorable outcomes often relies on whether a physician properly titrating their patients, that is prescribing a drug regimen that maintains therapeutic levels of the drug within the patient and typically adjusting or limiting the dosage or regimen to avoid unfavorable side effects. Advantageously, in one aspect, the system determines likely therapeutic levels of the drugs indirectly through various combinations of information that are accessible, without requiring test results. While the proper dosage and regimen may differ between patients, in some cases, a physician may not properly titrate the patients and the prescribed drug regimen may be sub-optimal such that the therapeutic effect of the prescribed drug is sub-optimal or eliminated entirely. A physician may fail to properly change a patient's dosing (dose titration) for any number of reasons, including lack of knowledge regarding the most recent clinical data associated with a given drug/treatment or a given patient population, lack of supply of the prescribed drug, and administrative or costing issues relating to the treated patient or associated health care service plan or insurer.

By use of the system to identify patients that were not properly titrating, suitable interventions were determined and carried out resulting in an increased rate of dosing approaching that of clinical studies and decreased unenrollments and discontinuation of treatments. Thus, field studies indicate that the system can identify patients that might otherwise have sub-optimal treatment early and improves patient outcomes in such cases or discontinue treatment as needed. In another example, in field studies, the system identified patients that were likely to discontinue early in treatment due to expected side-effects based on a combination of attributes associated with the patient. As an example, such attributes that could correlate to a patient falling off therapy for expected side effects could include; a prescription written with a very high starting dose and more than 1 refill, a patient that provides information to the pharmacist or Patient Advocate that they have no scheduled appointments or upcoming laboratory draws, a patient that is elderly. In each of these examples and specifically in combination, we have data that support higher likelihood of the common adverse events reported in clinical studies and therefore can provide preventative intervention. By determining suitability of an intervention in such cases and tasking one or more parties to outputting information in response directly to the patient and/or physician regarding expected side effects, patient compliance was shown to be improved.

In certain aspects, where the system identifies a consistent need for interventions, particularly where the need is associated with a particular field of information or with a particular patient population, the system can assess suitability of an intervention program, such as a patient compliance or patient advocate programs, and automatically enroll participants or output eligibility information for those patients to one or more parties. Field studies indicate that when the system revealed the suitability of such programs, enacting these programs results in a statistically significant decrease in discontinuation due to predictable side-effects. As an example, Patient Advocate Programs are in place to help patients better understand their disease, how to find correct specialists, how to deal with the challenges of treatment and identify resources (financial or otherwise) that may be necessary to support successful treatment of a patient. Patient Advocate Programs often assist patients by helping them to understand the biology of their disease and how treatments can specifically alter the course of that biology. In doing so, these programs collect a great deal of information regarding a patients education level on a disease state, the things that are of concern to them during the treatment process (cost, job stability, etc.) and their plan on working with their physician. The combination of many of these data points with data from other datasets can help identify potential risks in ways that other information sources.

While the above illustrate examples of fields of information used by the system to improve patient treatment and patient compliance, the system may further include various other fields of information, that may intuitively appear unrelated to patient outcomes from a treatment using a particular drug protocol. For example, the fields of information may include identification of an insurer or health care service plan or copay information. Such information may also be useful in determining suitability of interventions in various other aspects related to treatment, including administrative and business processes. By relating seemingly unrelated fields of information from different and/or disparate information sources, the system may determine a need for an intervention that might otherwise not be identified. For example, field studies indicated that various fields of information, such as geographical location, patient sub-populations or copay amounts, correspond to a perception by particular physicians that the patient cannot afford the treatment resulting in the physician providing the patients with lower doses in the hope of saving the patient money. An example of this is comparing dose and long-term drug adherence for patients that receive drugs through a free program versus those that receive drug that is paid for by their insurance. These data show that patients on free drug programs remain adherent to medicine longer and at higher doses at least two patient populations. In both of these instances, patients on free drug programs received higher doses of medicine than their counterparts on insurance, even when treated by the same physician. These situations lead to increased instances of non-titrating patients and sub-optimal patient outcomes. Since this relationship is particularly complex and may vary by physician, the system is advantageous in identifying the need for an intervention, as well as the most suitable type of intervention and on the level to which the intervention should be tasked. The system was able to determine an intervention for these particular physicians and task a third party, namely the drug developer, to communication with the physician the availability of financial programs to allow such patients access to proper doses at reduced costs. Timely determination and tasking of interventions by the system demonstrated an adverse selection bias in uninsured patients enrolled a free drug program. Analysis of patient compliance and patient outcomes in these cases demonstrate that uninsured patients on free drug program titrate at a much faster rate that closely resembles the clinical trials, refill their shipments on a more consistent basis and have comparatively longer durations on therapy at considerably higher doses than insured patient (see Table 1), thereby resulting in improved patient outcomes in subjects that would have otherwise likely experienced sub-optimal results or discontinued treatment. These uninsured patients, in many cases, demonstrated the best outcomes. Although the mechanisms by which the patients have improved patient outcomes may not always be understood, the system allows for identification and determination of outcomes to improve outcomes in both uninsured and insured patients, without requiring determination of a causal effect remains unknown. This aspect of the system and methods of the present invention is particularly useful, especially since the health care system involves complex and unpredictable interactions between multiple factors that vary widely between patients, physician and insurers. Such complex interactions will likely continue to develop in the foreseeable future.

Figure 4:
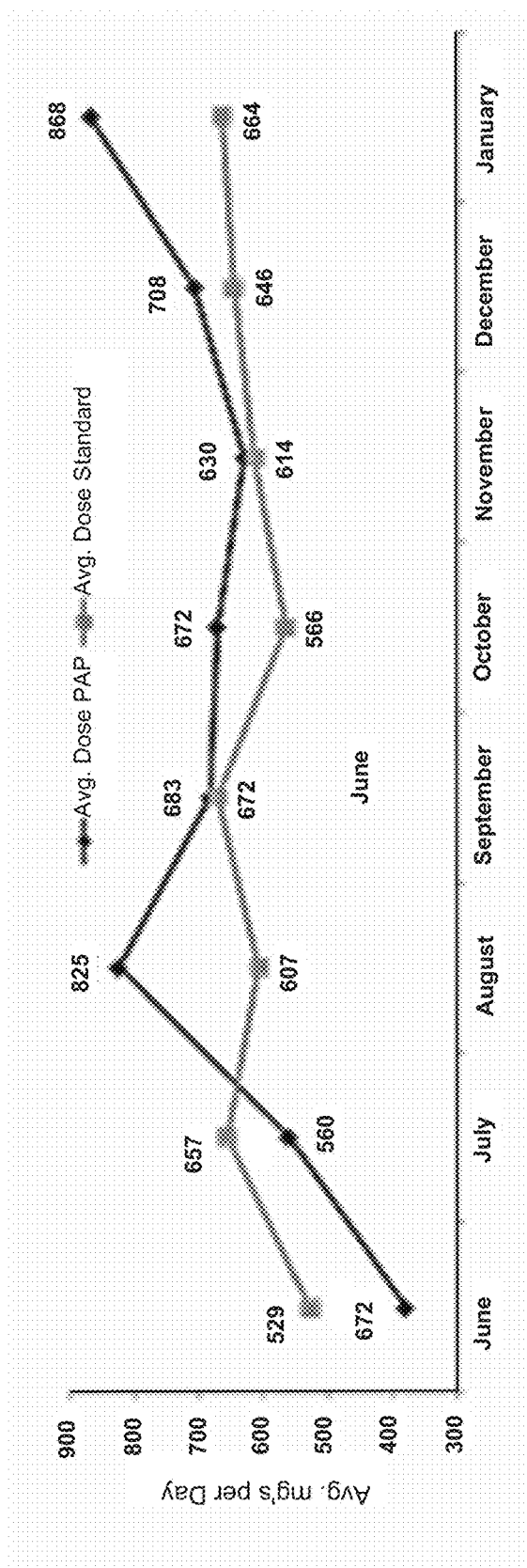
FIG. 4 illustrates an example relationship determined in an example embodiment, in accordance with methods of the invention.

One such relationship identified by an example embodiment of the system is illustrated in FIG. 4. By relating the average dose of various patient and relating the patients to a Patient Assistance Program (PAP), in which uninsured patients received drugs at no cost, the system reveals the patient on a PAP take consistently higher dose of the drug, such that the treatment outcomes of PAP patients are more in line with clinical studies. In contrast, the patients on standard treatment programs, in which insurance pays a portion of drug costs or a co-pay is required, indicate that such patients take consistently lower doses of the drug such that treatment outcomes tend to fall short of the results seen in clinical studies more often than the PAP patients. This aspect is but example of the unexpected relationships and trends identified by use of a system according to the present invention. As can be appreciated, relating these fields of information to various other fields of information (e.g. patient sub-population, physician, geographic location, pharmacy, age) may identify various other associations and suitability of interventions that might otherwise never be determined using conventional methods.

TABLE 1

Free Drug Treatment Program (PAP) versus Standard Treatment Program

| | October | November | December | January |
| --- | --- | --- | --- | --- |
| PAP Patients that filled Rx | 83% | 67% | 89% | 100% |
| PAP Patients not taking daily | 0% | 0% | 0% | 0% |
| Standard Patients that filled Rx | 83% | 82% | 68% | 65% |
| Standard Patients not taking daily | 17% | 10% | 14% | 17% |
| Standard fill rate (adjusted for non-daily use) | 100% | 92% | 82% | 82% |

In certain embodiments, the system receives multiple patient treatment attributes and associates one or more treatment attributes with certain aspects of the patient's treatment that may be used monitoring the treatment, and in improving and optimizing the treatment and patient outcomes. The patient treatment attributes includes one or more factors relating to the patient and/or the treatment, including but not limited to patient information, treatment information, geographical information, and health care services/administrative information. Patient information may include identifying information, demographics, geographic information, health related information, family and/or medical histories. Treatment information may include information relating to a particular treatment, drug regimen, pharmaceutical information, and information relating to drug administration, absorption and drug interactions. Health care services/administrative information may include physician information, physician treatment histories, cost information (e.g. copays, drug costs) and any information relating to a patient's health care service plan or insurance. The system associates one or more of these patient treatment attributes with a particular type of treatment and identifies the suitability of an intervention based on the association of the one or more patient treatment attributes with decreased patient compliance with a course of treatment and/or sub-optimal patient outcomes. An intervention may include modifying a patient's prescribed treatment, providing additional guidance to the patient, physician or third party relating to the treatment or administration thereof, so as to prevent reduced patient compliance or sub-optimal outcomes early in treatment, thereby improving patient outcomes in patients that might otherwise have been deemed unsuitable for treatment or suffered debilitating or deleterious outcomes.

In various embodiments, the system obtains a plurality of patient treatment attributes and associates certain attributes or varying combinations of attributes with decreased patient compliance or sub-optimal patient outcomes based an algorithm relating the attributes with decreased patient compliance and/or patient outcomes. These associations may be determined by the system according to a pre-determined algorithm input into the system, such as may be determined from patient studies of treatments obtained over time, or the system may be configured to perform a statistical analysis utilizing patient compliance information and/or patient outcome information input directly into the system. In the former approach, the accuracy of the system in identifying the suitability can be improved over time, for example by periodically updating the pre-determined algorithm as various associations become known through medical studies, while in the latter approach the system may continually identify associations even those that may be unknown or unlikely to be discovered in a formal medical studies. Various factors and combinations of factors may have complex interactions affecting the likelihood that a patient complies with a prescribed treatment or whether a physician prescribes or administers the treatment properly. For example, a geographic location of a physician may be indicative of a physician's reluctance to prescribe the most current treatment regimen, while the geographic location of the patient relative the drug supplier may an increased likelihood of lapses in compliance during treatment. Even if such information is known to a drug developer, health care administrator, or physician, these associations may not readily be evident, particularly when the association relies on a complex interaction between multiple factors. In addition, certain combinations of attributes may correspond to certain other unknown or unrealized factors that may adversely impact a patient's treatment such that these factors can be accounted for by the system. This aspect if particularly advantageous over conventional medical information systems and methods of treatment administration. This approach is especially useful for treatments utilizing drug regimens administered over a relatively long periods of time, and in particular, treatments using drug regimens where efficacy and tolerance of the drug varies considerably between patients, which may result in highly variable patient outcomes and/or reduced patient compliance. These difficulties, which may be pronounced in more vulnerable patient populations, can be reduced considerably or eliminated using the system and methods of the present invention so as to provide improved patient outcomes in patient that might otherwise have discontinued treatment or experience sub-optimal results.

An example of a treatment that can be difficult to manage due to less predictable patient response is administration of a synthetic steroid, such as mifepristone. Mifepristone is a synthetic steroid that binds progesterone and glucocorticoid receptors and has been employed to treat a number of conditions including meningioma, uterin fibroids, hyperadrenocorticism, and certain psychiatric illnesses. It has been surprisingly discovered that administration of the same dose of mifepristone can produce widely varying plasma drug concentrations in different patients. For the same dose of mifepristone, the plasma drug concentration can differ by as much as 800% from one patient to another. The varied plasma drug concentration can result in some patients not receiving an efficacious dose of mifepristone. For these patients in particular, it is necessary to improve the pharmacokinetics of mifepristone upon administration. Treatment with mifepristone can be further understood by reference to the following commonly-owned application: U.S. application Ser. No. 13/677,465 filed Nov. 15, 2012 entitled "Optimizing Mifepristone Absorption," the disclosure of which is incorporated by reference in its entirety. It is understood that the methods and systems of the present invention may be used in variety of treatments, and are particularly advantageous when used with complex and difficult to manage treatments, such as any therapy that requires dose titration over time. The length of such therapies may extend over a period of weeks, months, a year or many years.

An example of this difficulty could be shown with glucocorticoid receptor antagonists, which involves blocking the activity of a certain type or types of hormones at a receptor level. A consequence of doing this causes an imbalance in the systems within the body. Patients will become tired, fatigued and nauseous as their bodies have become accustomed to high doses of steroids on a chronic basis. Blocking the activity of these steroids leads to a feeling of withdrawal, similar to the effects that a patient feels when trying to stop taking recreational drugs that they have become addicted to. In addition to these effects, the concentration of the hormones in the body remains very high since the activity of hormone production is not altered. This can cause additional effects on other systems that need to be monitored and controlled. A specific affect that is noted by glucocorticoid antagonists is that the hormones that are blocked can flow to other systems within the body and create excess activity on the mineralocorticoid receptor (which is unblocked). This activity can cause patients to have significant swelling and reductions in potassium levels, potentially to dangerous levels. Without the proper use of mineralocorticoid antagonists in combination with glucocorticoid antagonists and finding a new balance with each titration, patients may never benefit from the therapy. Another example of a difficult to manage therapy is chemotherapy, which often involves administration of chemotherapy agents in a treatment regimen over three months or more and require tight adherence that may benefit from timely interventions. These are but a few examples of difficult to manage aspects of treatment that are not adequately addressed by conventional treatment methods and that may benefit from application of a treatment system and methods in accordance with embodiments of the invention.

In certain embodiments, the system analyzes the fields of information using one or more algorithms input by a user. Such algorithms may incorporate relationship or information obtained through clinical studies, or may relate to various other concerns, such as business or administrative processes. An example of a specific algorithm is described as follows: a prescription written at a low dose with 12 refills is interred into a patient's medical information maintained by their physician or medical facility, upon entry by the pharmacy, the system identifies that the patient does not have a physician follow-up, which triggers an intervention determination and tasking of the intervention to a Patient Advocate of an indicator to initiate contact with the patient and/or physician to obtain more information about follow-up, such as potassium and blood draws for laboratory work. The system receives confirmation by the Patient Advocate of the risk necessitated intervention and tasks the Patient Advocate with another task (e.g. directed the patient to speak with the physician regarding the follow-up laboratory blood work. The system then tasks a field representative to provide information regarding the follow-up laboratory work to the physician. In some embodiments, the system creates a hold at the pharmacy so that the pharmacist is required to contact the physician to discuss the follow-up laboratory results and discuss any adverse events before filling a subsequent prescription, particularly when the subsequent prescription involves a change in dosage.

As can be understood in the above example, a particular intervention may include multiple aspects performed according to a particular timing and/or sequence, in order to adequately address the risk associated with the determined intervention. In this example, the first task of the intervention was to determine whether follow-up blood work was planned, the second task was to notify the patient to contact a physician or medical personnel regarding follow-up, the third task was to provide additional information regarding follow-up to the physician by an indicator sent to a field representative, and the fourth task was to obtain additional information from the physician regarding the follow-up laboratory work by the pharmacist, which was effected concurrent with a hold placed on the prescription refill. In one aspect, these different tasks are effected in a particular sequence according to a particular timing, such as within 1-2 weeks, so as to adequately address the risk triggering the intervention within a suitable time frame for a given treatment (e.g. within the window of a single prescription). Advantageously, such a configuration allows the treatment to be properly titrated, while avoiding lapses in medication between prescriptions or undesirable changes in dosage. By coordinating multiple tasks output to multiple different entities, each associated with a different information system (e.g. pharmacy, medical facility), the system allows for improved efficacy of difficult to manage treatments. As many pharmacies, physicians and medical facilities have become overburdened with management of information, such a system can become invaluable for a difficult to manage treatment, such as a treatment with glucocorticoid receptor antagonists.

Figure 5:
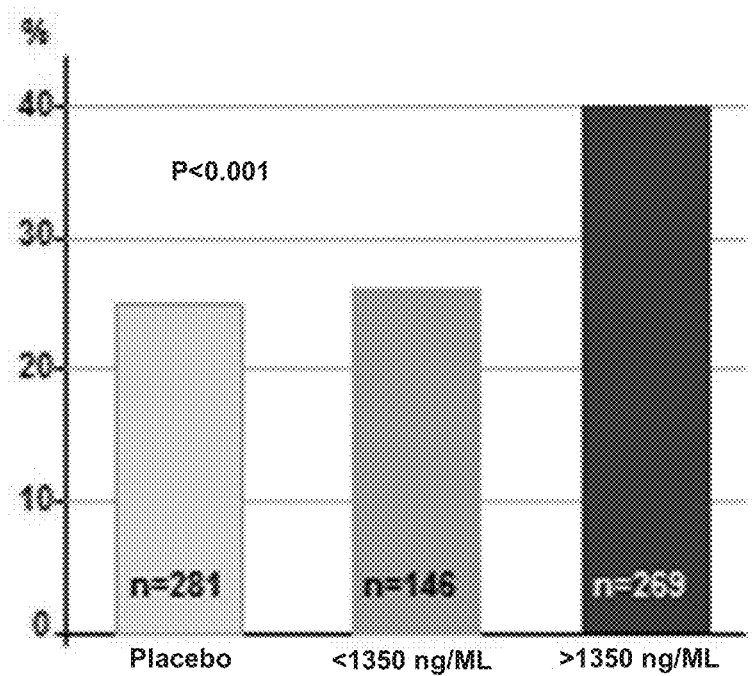
FIG. 5 illustrates an example relationship determined in an example embodiment.

Examples of information that may be utilized within such systems include drug information relating to the drug treatment of concern. For example, studies indicate that in administration of mifepristone, plasma levels within the patient drives the drug response. This relationship is illustrated in FIG. 5. By including this relationship within an algorithm of the system, the system may identify fields of information, or combinations thereof, that correspond with insufficient plasma levels. Such factors may relate to insufficient titration, low dosages, patient attributes, age, diet, through various interactions that may be undetermined. Utilizing the system to store, relate and analyze such factors, however, allows the system to monitor various factors and intervene as needed to ensure appropriate plasma levels are maintained and facilitate optimized treatment outcomes. Advantageously, the system may provide these benefits even without identifying the relationship to plasma levels or that the plasma level was the factor at issue. This relationship demonstrates some of the complexities and challenges associated with a treatment utilizing administration of a drug that the present invention addresses to further improve such treatments, particularly in vulnerable patient sub-populations.

Patients utilizing mifepristone to treat medical conditions require intensive follow-up to achieve optimal care and resolution of symptoms, which can lead to variable patient outcomes. Patients in which intervention may be needed to ensure optimal treatment can be difficult to identify before treatment is either discontinued by the patient or by the physician. This difficulty is due partly due to the manner in which the pharmaceutical data, medical information, and patient information is obtained and maintained. In conventional system, such information is maintained by various separate entities and, even when such information resides in a common repository, the data remains largely unrelated. For example, although pharmaceutical manufacturers provides a substantial amount of data regarding a particular pharmaceutical, which even if provided to the patient or maintained in a system by the physician or medical provide, remains unrelated and unassociated. This may be due partly to the highly unrelated nature of most pharmaceutical manufacturer data provided.

Similarly, various other factors or combinations of factors associated with differing fields of seemingly unrelated information may have considerable effects on treatment that would be difficult to predict. Regarding fields of information relating to an associated pharmacy may affect patient compliance or treatment efficacy, particularly in treatment indicating GR-II antagonists, since different pharmacies operate in different manners. Another field of information that may cause an effect in some cases, either directly or indirectly is the location of delivery. For example, the system may utilize this information by mapping the location of the delivery to the location of the prescribing physician. For some patient populations, this may be used to determine the likelihood of a patient to make frequent visits to their physician for checkups and lab work. While some physicians draw patients almost exclusively within 30 miles, other physicians, particularly those at teaching institutions, may have no patients within 500 miles. By analyzing such information, the system can determine the suitability and type of intervention on a physician level or a patient level. For example, one such intervention may be to conduct an outreach to an affected patient and to ensure a local physician is available to monitor the patient's signs, symptoms and key blood levels and offer patient support. In some embodiments, the system may provide an automated intervention to such patients and recommend physicians that may be closer to them geographically to monitor basics in-between visits to their primary prescriber or recommend an appropriate outreach program In various embodiments, the system may utilize any number of algorithms to determine statistical relevance of one or more fields or combinations of fields to a result, the result being associated with one or more of patient compliance, patient outcomes, treatment or various business related aspects. By applying statistical analysis, the system can determine the likelihood that a result or relationship is caused by something other than mere random chance so as to determine if the field of information or combination of fields is statistically significant to the desired result. The analysis provides a "p-value" representing the probability that random chance could explain the result. In general, a 5% or lower p-value is considered to be statistically significant, although the threshold of significance and desired confidence level may be selected or varied as desired to facilitate a desired result or identify information or relationship relating to a desired attribute or business concern.

In certain embodiments, the system may utilize an algorithm that apply a known or predicted association between one or more fields and a result that is input by a user or included in a system update. Such algorithms may be determined periodically as associations are identified through clinical studies or otherwise. In some embodiments, the system may apply statistical analysis to determine associations between one or more fields and a result in addition to applying an algorithm input into the system such that the statistical analysis of various fields of information can be reassessed as various other associations are identified over time. These features provide further improvements as ever more complex interactions between the fields of information can be identified and interventions tasked to inhibit or reduce adverse effects associated with such interactions.

V. Part D: Identifying and Assigning Human or Computer Intervention

Once the need or suitability of an intervention is identified by the system, the system may select a particular type of intervention based on data relating to the patient and/or treatment, which may include any of the attributes or data factors described herein. The data information stored and/or access by the system is used to select or determine the most effective form of intervention for a given condition. This selection of intervention type may be based on a data requirement or algorithm input by the user or may be determined by the system based a relationship between one or more of the data factors and success of past interventions associated with the same or similar data factors. In addition, this selection/determination of intervention type may utilize an algorithm so as to determine the most suitable type or form of intervention based on a complex relationship between multiple data factors.

By identifying the need for an intervention and providing a timely intervention, patient compliance can be improved and/or treatment can be optimized to improve patient outcomes. In addition to determining the suitability of an intervention based on the data and/or data relationships, the system identifies an appropriate party to perform the intervention and tasks the identified party to perform the invention. The intervention may include a communication by phone, e-mail, or any suitable means to any entity associated with the treatment and/or patient (e.g. a physician, health care administrator, pharmacy, patient or caretaker, or third party). The intervention may be performed by any of the above entities or by an automated unit of the system (e.g. automated text, voicemail, or e-mail reminders or alerts). In addition, the system may track the status of the intervention, monitor the result of the intervention and/or follow-up on the status of the intervention to ensure it was performed timely. Timely intervention based on these data will help to improve patient care. The methods and system of the present invention are particularly useful in providing optimal care for patients undergoing a treatment utilizing a drug regimen, such as mifepristone, that requires intense physician and patient follow-up due to the nature of the medicine.

Various types of interventions have been identified to serve a variety of needs. For example, an intervention may relate to delays in processing or delivering shipments of a drug to a medical facility or to a patient such that a drug manufacturer or developer may be tasked to initiate an intervention to the drug supplier/delivery facility to ensure timely drug shipments. This aspect optimizes not only the business transactions between these entities, but may improve patient compliance and treatment through timely and consistent drug delivery. In various embodiments, the need of an intervention is determined by the system using a relational database system without requiring the fields of information actually be stored on the system. With the combination of the relational database system and the data requirements and/or algorithm associated with a particular entity, the need for an intervention can be timely identified, specific interventions can be created and tasked or assigned to an appropriate entity and followed to completion. If the tasked intervention is not timely completed or the data obtained after the intervention is indicative of intervention failure, this may trigger another intervention, which may relate to the original interventional condition, or to the tasking and intervention process itself. For example, if the intervention proves unsuccessful or is not timely performed by a first party tasked with the intervention, the system may indicate an alternative intervention to address the original intervention condition or may task an intervention to a second party to perform the intervention and/or remedy the failure of prior tasked intervention. Thus, in some embodiments, the system determines multiple tasks to differing multiple entities according to a particular sequence and timing so as to ensure a risk associated with a determined intervention is adequately addressed.

In certain aspects, tasking is performed through email but can be modified and automated in various ways if desired. Tasking may include any identifier of a task (e.g. indicator light, e-mail, text). For example, should the system determine that a physician does not regularly titrate patients, the system identifies a need for intervention(s) on a physician level and task the intervention to address the problem. Such tasking may include an automated task performed by the system, such as e-mailing the primary contact for the physician to check a report highlighting the physician's challenges with proper titration and/or sending an e-mail with the report to a sales person instructing the sales person to make an appointment with the physician to discuss dosing and titration. As discussed above, plasma level response of an administered drug correlates with dosing, which may vary considerably between drugs. Although plasma level response in response to dosing may vary between patients and various factors, improving proper dosing and titration generally results in improved patient outcomes more in line with clinical results. Thus, by determining the need for and tasking interventions on a physician level that relate to dosing and titrating, the system allows for improve plasma level response in treated patients, in turn, improving patient outcomes. The system further improves the above noted correlations as additional factors that may relate to variations in plasma level response (e.g. sub-populations of patients, treated condition) may be identified and the interventions adapted accordingly. Completion of these tasks may be recorded by or input into the system as another field of information and associated the physician information within the system.

In some embodiments, the system is configured to identify suitable patients for a particular treatment through various resources, such as online questionnaire or patient advocate programs provided by a developer of the treatment, and determine whether the patient's physician had previously received information regarding the treatment. The system may identify when such a patient has an upcoming appointment as a situation in need of an intervention and task a field personnel to conduct physician outreach to educate the physician on the treatment prior to the patient visit. When used in this manner, results indicated that the identified patients were more likely to be enrolled in the treatment by their physician than in patients where no intervention occurred.

The above aspects are further illustrated by the following example embodiments of the invention. According to one example, if a physician has not increased the dose of a patient's medication to a level that will likely generate a therapeutic effect, such as may be determined from patient studies or from patient monitoring data received by the system, the system identifies that an intervention is needed to adjust treatment. The system then proceeds to select/determine the appropriate intervention(s) and task the determined intervention(s) to the appropriate party or parties. As can be understood by the complexities of the relationships between various data factors, a given interventional may include multiple tasks by one or more parties or entities. Examples of these tasks might include: tasking a third party pharmacist to reach out to the physician and patient to discuss potential changes to their prescriptions, tasking a manufacturer representative to contact the physician to set up educational information, tasking a patient specific program to call the patient to discuss the drug (e.g. mifepristone), tasking a system to generate an email or fax to the office or prescriber requesting an updated prescription, or various other tasks. By use of this system according to the methods described herein, the information is utilized to ensure optimal care of patient undergoing treatment, particular treatment involving a drug regimen requiring careful monitoring and administration, such as mifepristone.

VI. Application

By accessing one or more fields of information from various sources and relating the one or more fields to indicators of success or failure in patient compliance and/or treatment efficacy, the system allows for identification of a need for an intervention from seemingly unrelated fields of information. Moreover, these fields of data can be analyzed on various different levels and, in turn, the resulting interventional alerts may be output on various different levels. For example, one or more fields of information may be analyzed in relating one or more other fields of information and assessed in terms of patient compliance and/or treatment efficacy. For example, a patient dosage field may be related to a physician last name field and these combinations associated with patient compliance and/or treatment efficacy. Associating these data relationships may reveal that a particular physician is not properly titrating (e.g. not sufficiently monitoring and adjusting dosages according to each patient). By analyzing these relationships on a physician level, the system can determine a need for an intervention on a physician level (e.g. an alert to a physician or to a third party to communicate with the physician) to address and remedy the physician is not a significant factor in non-titrating patient, which may indicate that various other factors or fields of information, may require analysis to determine whether an intervention is suitable. For example, patients in a remote geographical location or patients having higher co-pays may not be properly adhering to an prescribed dosage such that the system may determine a need for an intervention on a patient level or on an insurer level. Alternatively, a determination of a reduced patient compliance or treatment efficacy on one or more levels may trigger an intervention on one or more of the same or different levels. In certain aspects, the result of an intervention alert is received as yet another field of information, such that the determination of an intervention and the type and level of intervention determined can be analyzed and further optimized based on success or failure of past interventions.

To further illustrate these concepts, use of the system is described in regard to a determined relationship between dosage and shipment data analyzed on a physician level. When the drug is supplied to the patient directly by the drug developer or manufacturer, the system can utilize shipment data to determine an actual dose received by the patient, even when the actual dose received by the patient differs from the prescribed dosage. For example, if a shipment includes a 30-day drug supply at 300 mg/day, the shipment data can be analyzed to determine a patient's treatment dosage, as well as changes in the dosage over time. Typically, one shipment includes a 20-day supply with most patients taking one to four tablets each day (300 mg-1200 mg). By associating the dosage data with the patient's physician, analysis and intervention is performed on a physician level, as shown in FIG. 6B, allowing the system to identify physicians whose dosing falls below therapeutic levels as determined by clinical data. The system then uses this information to identify where an intervention is needed, select or determine appropriate intervention(s) and task the appropriate party or entity to perform the intervention. In determining the suitability of an intervention on a physician level, the system may further include various other factors relating to the physician, such as the level of experience of the physician, physician history, and geographic information. These factors can be used to determine whether an intervention is needed, as well as what type or form of intervention is most appropriate. For example, each physician may be rated as "experienced" or "not experience" or ranked on a scale based on their previous experience with a particular drug treatment and whether the physician has a history of successfully treating patients with the drug. If a physician is experienced with a particular drug treatment, the system may apply higher triggering thresholds for indicating an intervention condition. If the physician is less experienced, the physician may be less likely to titrate patients properly, which may lead to lower efficacy, shorter duration on therapy and decreased patient compliance. When the physician is less experienced, the system may use a lower threshold to trigger for indicating an intervention condition and may determine different types and forms of interventions than would be indicated with an experience physician. When the physician is less experienced or when there is insufficient physician information, the system may analyze additional factors when determining whether an intervention condition is present. For example, such as monitoring of prescription data information (e.g. number of refills at non-titrating doses). The number and type of interventions determined may also differ according to the experience of the physician. For example, when the physician is more experienced, an electronic communication (e.g. e-mail, text), may be adequate, while when the physician is less experienced, the system may output an alert to field personnel to initiate closer contact with the physician and/or patient by phone or in person to discuss treatment and possible side effects. Such interventions may be necessary in these circumstances, since such physicians may be more likely to overreacts to any adverse events or side-effects experienced by the patient and potentially discontinue the therapy before efficacy can be realized. In addition, the intervention may include contact and communication directly with the patient by any of a patient advocate, nurse, pharmacist, administrator, and reimbursement service provided so as to educate the patient or address potential concerns thereby improving likelihood of patient compliance and successful outcomes of treatment.

Figure 6A:
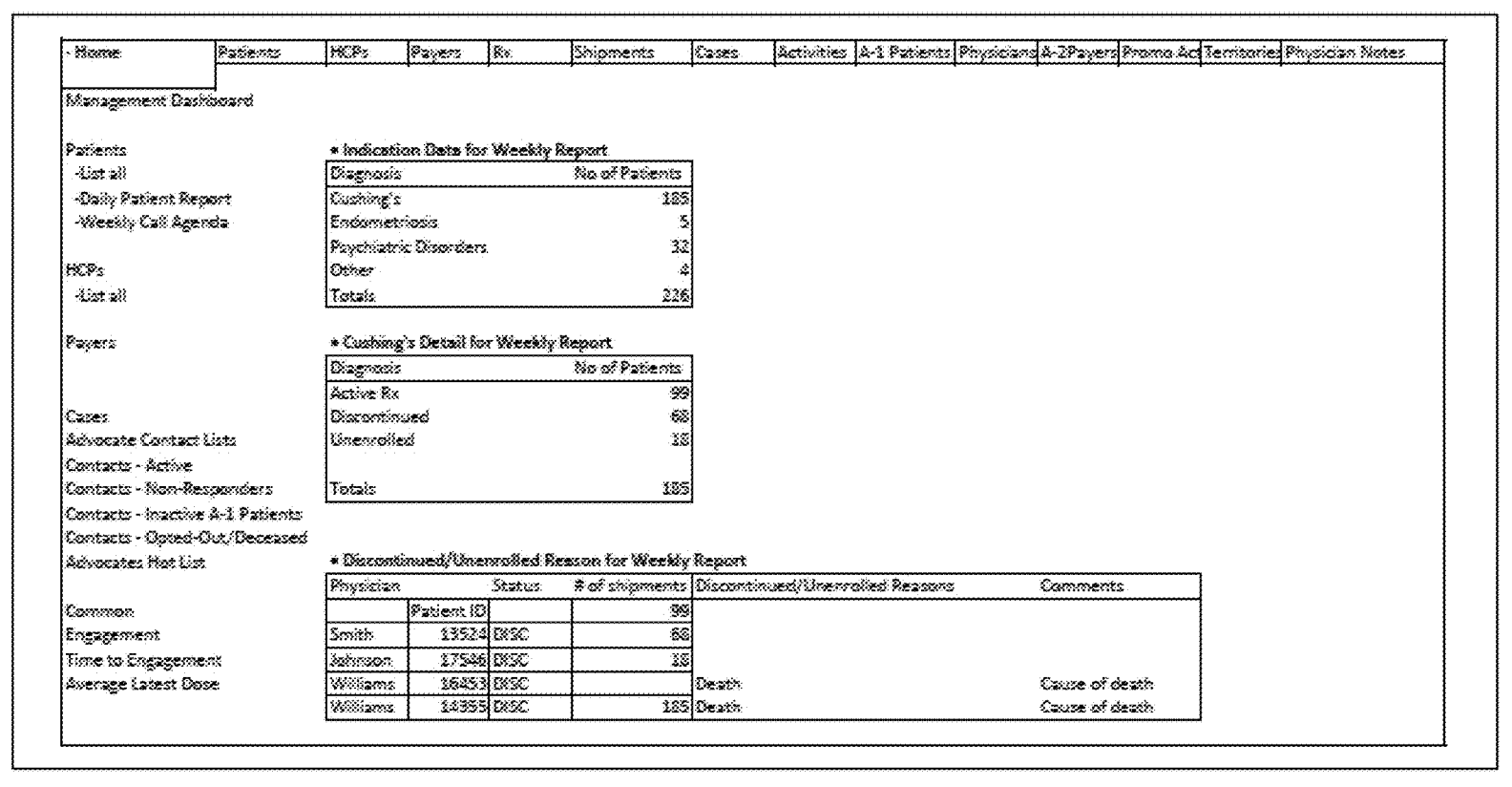

As can be understood by the examples above, the data requirements and algorithms that trigger a determination of an intervention condition can be quite simple or fairly complex. For example, multiple shipments of low doses or single shipments at very low doses can trigger an intervention to contact the prescribing physician and request more information regarding the treatment or to educate the physician on recommended dosages. The system may also be configured to perform a considerably more complex analysis of factors, such as tracking the shipments to various patients over time, determining likely doses by the patient and analyzing which patients fall above or behind the titration curve of the general population based on results from clinical studies and/or the curve of a specific physician. Such analyses allows the system to identify patients that may be outliers early in treatment and through the intervention and tasking processes described above, provide additional monitoring and attention to those patients that might otherwise experience sub-optimal outcomes. In another aspect, the system may associate various other fields of patient information, including demographic information, health information and disease state or severity, such that the system can identify potential sub-populations requiring interventions to improve patient outcomes In certain aspects, the system is configured with a user interface that displays the information output of one or more fields of information in response to a request or search entered by a user. One such example is illustrated in FIG. 6A, which lists a weekly report of indication data, and a detail for patients being treating for Cushing's syndrome and a weekly report for discontinued/unenrolled patients. Such reports may be automated or may be customized by a user as desired. These information outputs may be used by the system in identifying an intervention, determining a suitable type of intervention or tasking the intervention and may assist the user for various other purposes or business concerns, such as budgeting, forecasting and planning.

In the example illustrated in FIG. 6B, physician Smith's patient is receiving improperly prescribed 50% of the recommended dose, while Johnson and Williams appear to have discontinued treatment after only two months. Upon identifying the physicians at risk for administering sub-optimal treatments as a condition suitable for an intervention, the system determines an appropriate intervention and tasks the appropriate party/entity. For example, the system may output an alert to the drug developer/manufacturer to communication with physician Smith and provide information or counsel to physician Smith as to the recommended dosages or the intervention may be automated such that the system automatically send an electronic communication (e.g. text or e-mail) to physician Smith or associated staff personnel that the prescribed dose is likely to fall below therapeutic levels or that the patient is delaying ordering refills and is likely not taking the drug at the prescribed dose. The system may utilize the same or similar interventions to communicate to physicians Johnson and Williams that two months is insufficient duration to assess suitability or efficacy of the drug treatment or lack of compliance by the patient. In response, the system determines whether an intervention is required, and tasks the intervention through one or more tasks that are tasked to one or more different entities according to a particular sequence and timing so as to improve treatment efficacy and patient compliance by avoiding undesirable lapses in medication or changes in dosage that may adversely affect treatment.

An example information output report provided by the system is shown in FIG. 6C. Such information may be returned in response to a request or search by a user, or may be automatically provided within a tasked intervention to provide the tasked entity with relevant information to understand and perform the tasked intervention. For example, in response to received data indicating that a dosage of 300 mg/day is needed for a duration of at least four months to ensure that the patient receives therapeutic levels of the drug in order to assess the efficacy of the treatment, the system may analyze the stored and related fields of information and identify the need for an intervention on a physician level and output the relevant information within a tasked intervention as to which physicians are failing to properly titrate their patients. Alternatively, if analysis of the fields of information indicates lapses or delays in ordering refills that may be indicative of reduced patient compliance, a tasked intervention may include contact with the patient, enrollment in a Patient Advocate Program or interfacing with the insurer to address administrative or cost concerns.

In an example embodiment, the system may monitor and track the number of shipments of a particular drug to a physician over time and associate this shipment information with the number of patients treated with the drug by the physician to determine whether the physician is properly titrating their patients, without ever directly receiving prescription information from the physician. In another aspect, if the shipments are shipped directly to the patients, the system can determine which physician require an intervention by determining a patient's dosage based on the number of shipments over time and associating this data with their physician. Current studies indicate that dosing has a significant correlation in clinical trial response and that dosing correlates with plasma level response for various conditions, in particular treatment of psychotic depression. Current studies further indicate that patients that receive four shipments exhibit substantially higher patient compliance during treatment, take higher doses, and exhibit results in line with clinical studies and indicate improved outcomes based on subjective third party discussions.

In another aspect, the system provides access to the field(s) of information such that the fields can be viewed and sorted according to one or more fields or combinations of fields or on or more levels (e.g. physician, patient, insurer, type of treatment). This feature allows a user to access, organize and analyze information for various purposes. Such features can be particularly useful for administrative and business purposes, such as development of free drug programs and patient advocate programs to planning and shipments of drug manufacturing and shipping. The system may be configured with a user interface that allows a user to create a custom report that may be used for various purposes. For example, the custom reports may be used to identify optimal data requirements or relational algorithms that may be of use in further clinical studies or may be of interest to various entities utilizing the system. In addition, the custom reports may be useful for analysis any factor relating to treatment or to analyses various other factors, including transaction, administrative and business processes.

Figure 7:
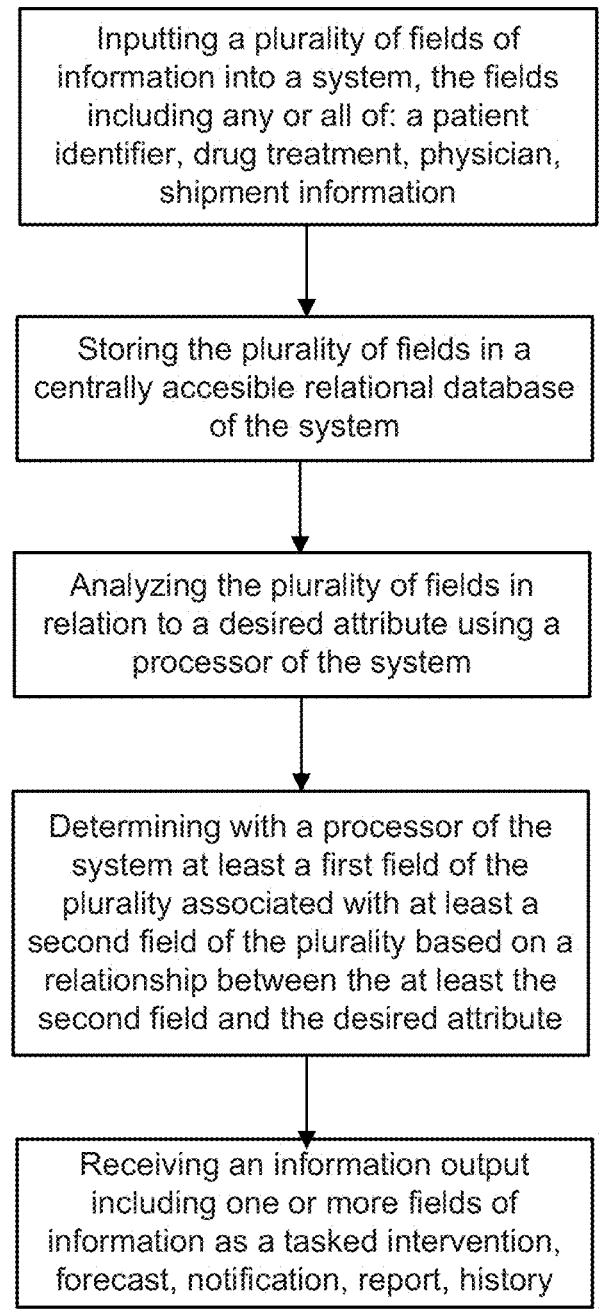
FIGS. 7-11 illustrate example methods in accordance with embodiments of the invention.
Figure 8:
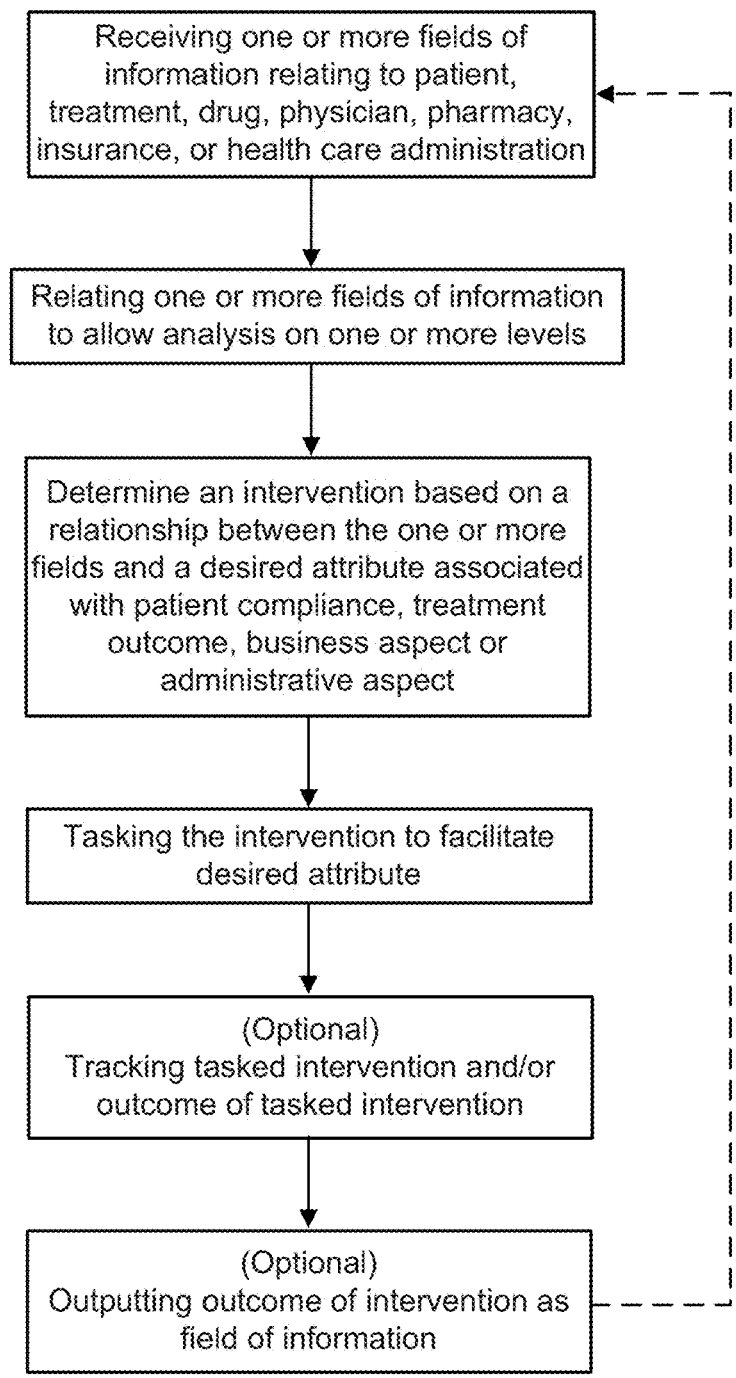

Example methods in accordance with the present invention are illustrated in FIGS. 7-8. In the example embodiment of FIG. 7, the method includes a user inputting a plurality of fields of information into a system, including but not limited to information relating to the patient, physician, drug, drug treatment, insurer or various shipping or administrative process. The plurality of fields of information are then stored by the system, such that the fields of information are centrally stored or are otherwise centrally accessible, and relates the fields with one another such that the fields of information can be analyzed to identify suitable interventions using a processing unit of the system. A user then determines a first field (e.g. patient info) based on a relationship between at least a second field (e.g. physician and/or drug) associated with the first field and a particular attribute or outcome (e.g. treatment outcome) using a processor of the system and one or more algorithms of the system. The user then receives an information output from the system with one or more fields of information, which may be in the form of a tasked intervention, a forecast, a notification, report or history. It is understood that this method may include any of the variations and features described in any of the embodiments described herein.

In the example embodiment of FIG. 8, the system receives one or more fields of information relating to a patient, physician, pharmacy, insurance or health care administration; the system then relates the one or more fields of information allowing analysis on or more levels. The system then determines an intervention based on a relationship between the one or more fields of information and a desired attribute or outcome associated with patient compliance, treatment outcome or a business or administrative aspect. The system then tasks the intervention to an appropriate entity, as determined by the system, to facilitate the desired attribute or output information relating to a desired attribute. Optionally, the system may be configured to track the tasked intervention and/or the outcome of the tasked intervention to ensure the intervention is performed and, optionally, the outcome of the intervention may be fed back into the relational database as an additional field of information so as to inform and improve treatment.

Figure 9:
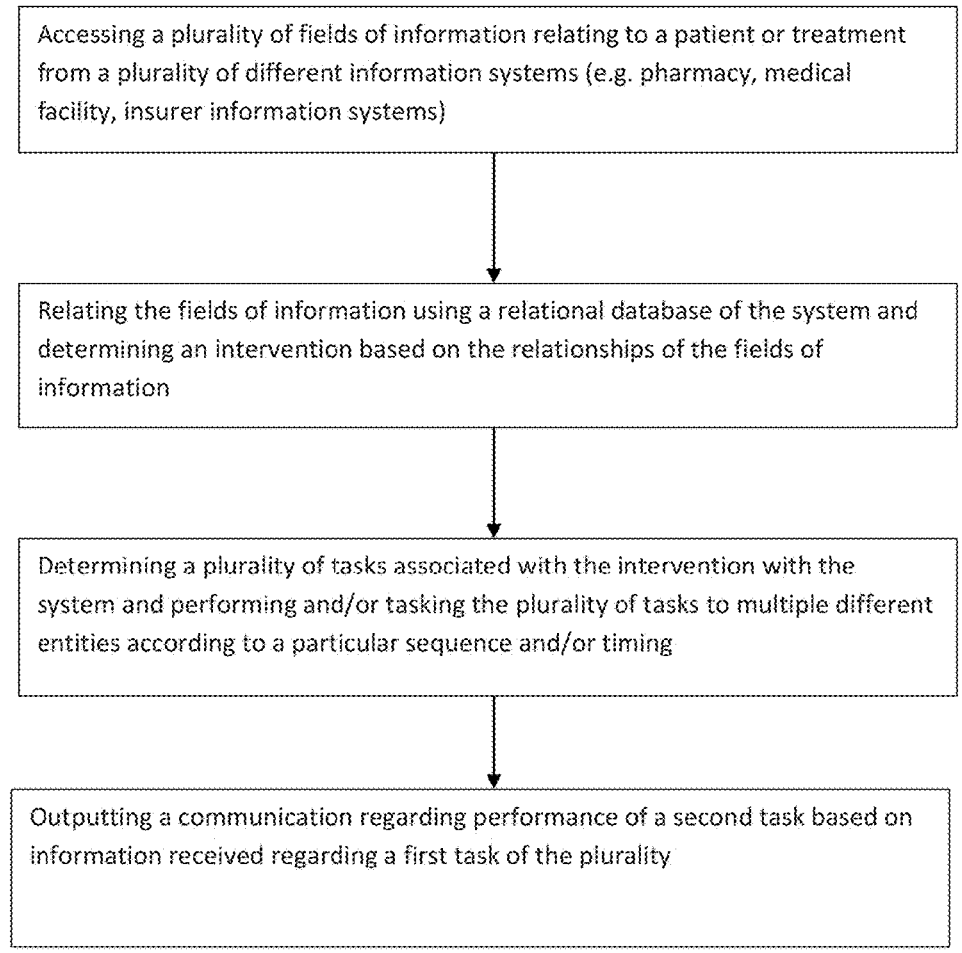

In the example embodiment of FIG. 9, the system performs a method that includes steps of: accessing a plurality of fields of information relating to a patient or treatment from a plurality of different information systems (e.g. pharmacy, medical facility, insurer information systems); relating the fields of information using a relational database of the system and determining an intervention based on the relationships of the fields of information; determining a plurality of tasks associated with the intervention with the system and performing and/or tasking the plurality of tasks to multiple different entities according to a particular sequence and/or timing; and outputting a communication regarding performance of a second task based on information received regarding a first task of the plurality.

Figure 10:
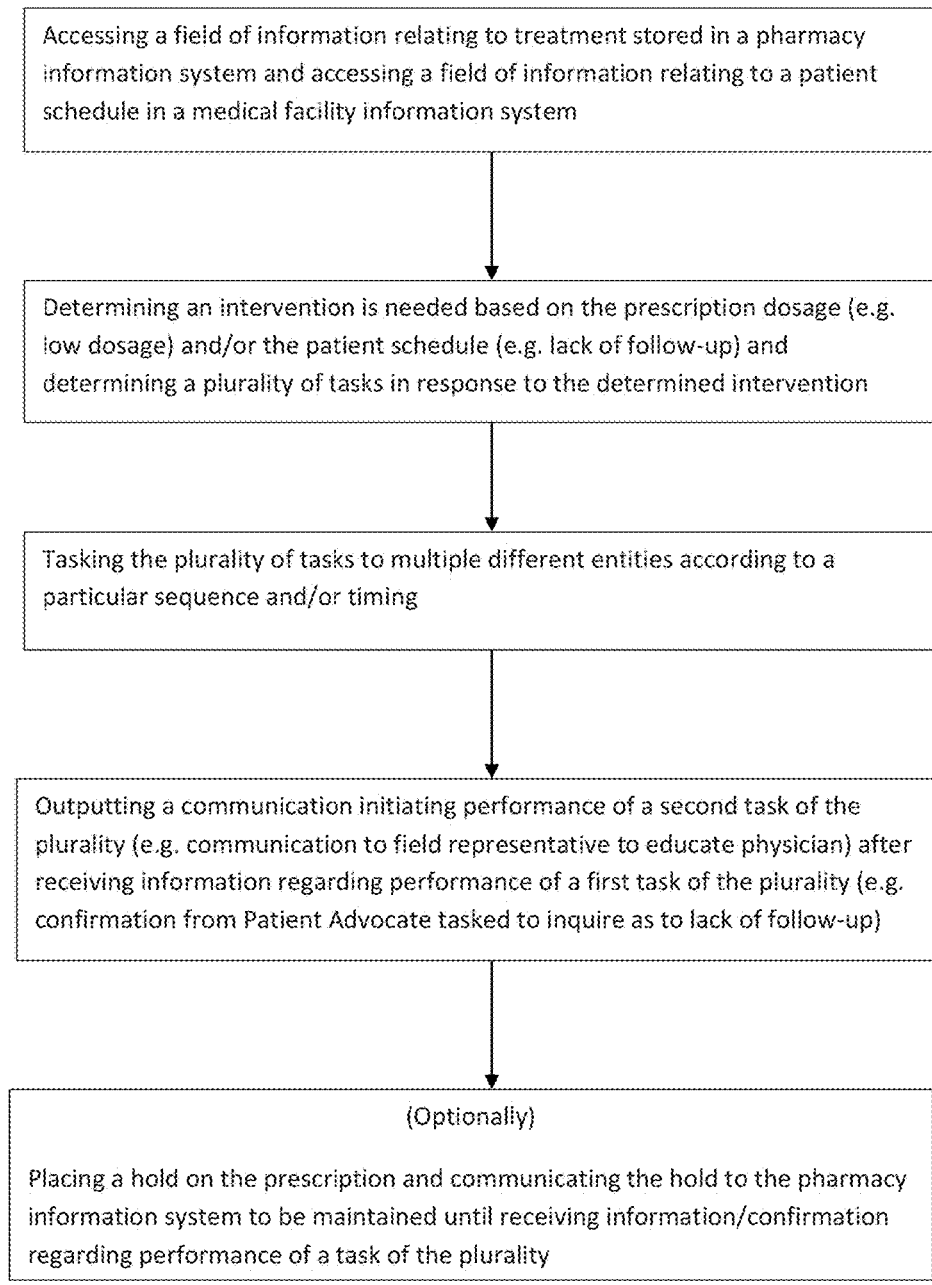

In the example embodiment of FIG. 10, the system performs a method including steps of: accessing a field of information relating to treatment stored in a pharmacy information system and accessing a field of information relating to a patient schedule in a medical facility information system; determining an intervention is needed based on the prescription dosage (e.g. low dosage) and/or the patient schedule (e.g. lack of follow-up) and determining a plurality of tasks in response to the determined intervention; tasking the plurality of tasks to multiple different entities according to a particular sequence and/or timing; outputting a communication initiating performance of a second task of the plurality (e.g. communication to field representative to educate physician) after receiving information regarding performance of a first task of the plurality (e.g. confirmation from Patient Advocate tasked to inquire as to lack of follow-up); and placing a hold on the prescription and communicating the hold to the pharmacy information system to be maintained until receiving information/confirmation regarding performance of a task of the plurality.

Figure 11:
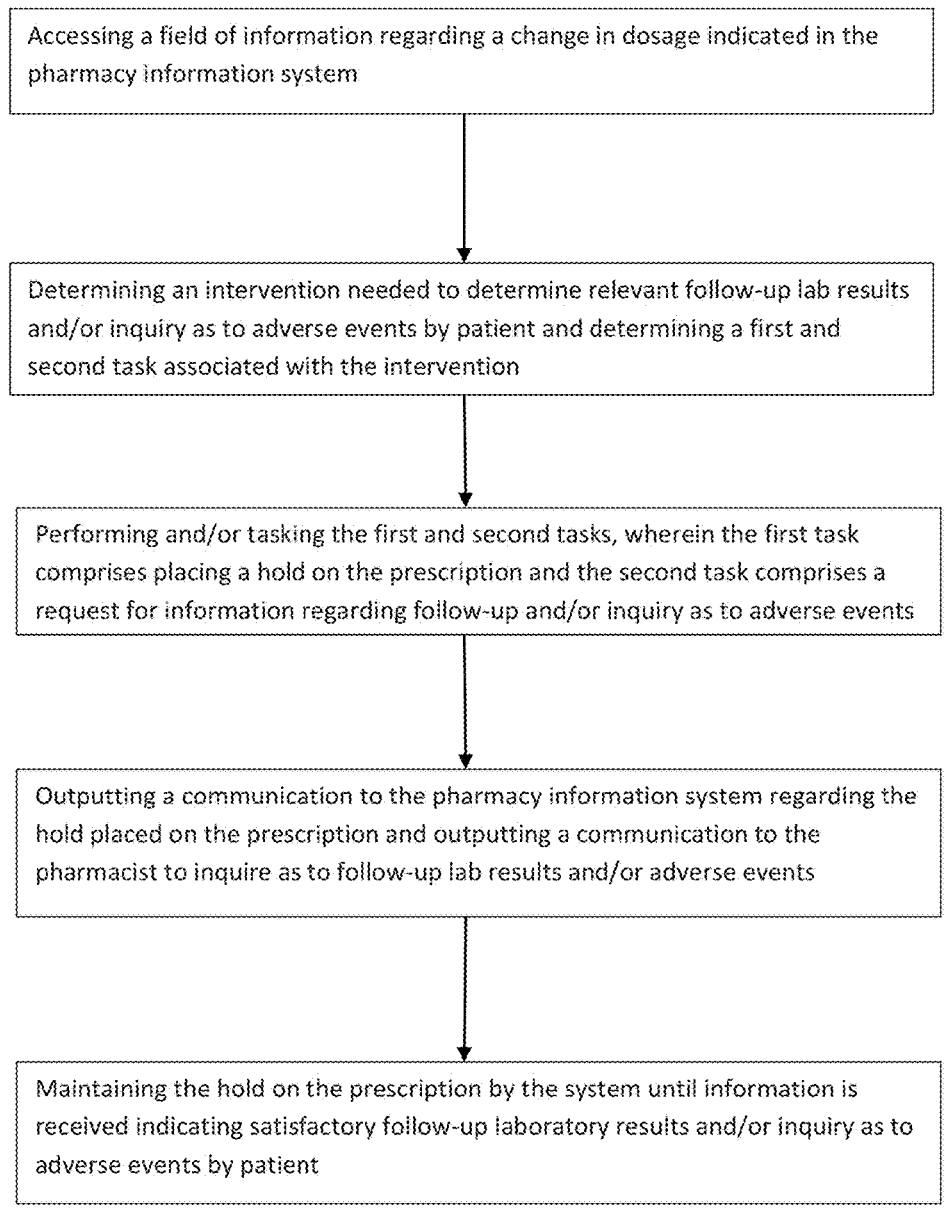

In the example embodiment of FIG. 11, the system performs a method including steps of: accessing a field of information regarding a change in dosage indicated in the pharmacy information system; determining an intervention needed to determine relevant follow-up lab results and/or inquiry as to adverse events by patient and determining a first and second task associated with the intervention; performing and/or tasking the first and second tasks, wherein the first task comprises placing a hold on the prescription and the second task comprises a request for information regarding follow-up and/or inquiry as to adverse events; outputting a communication to the pharmacy information system regarding the hold placed on the prescription and outputting a communication to the pharmacist to inquire as to follow-up lab results and/or adverse events; and maintaining the hold on the prescription by the system until information is received indicating satisfactory follow-up laboratory results and/or inquiry as to adverse events by patient.

While the examples described above are illustrative of some of the basic concepts described herein, it is appreciated that these advantages extend to risk factors and interactions between risk factors that are far more complex, which conventional treatment methods fail to recognize or address and might otherwise prevent a number of patients from receiving optimal treatment. The above described embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A method of treatment of a Cushing's syndrome patient using a drug protocol with a system having a relational database and a processor, the system being coupled to one or more electronic devices, wherein the drug protocol comprises administration of mifepristone to said Cushing's syndrome patient, the method comprising:

accessing one or more fields of information from a plurality of differing information systems accessible by the system, wherein the plurality of fields of information includes any of a patient identifier, patient characteristic, treatment regimen information, drug dose information, drug refill history, symptom reporting, patient or physician communication, or any combination thereof;

identifying, with the system, patients or their physicians having need for an intervention for achieving a desired result, wherein said identifying need for an intervention comprises identifying, without requiring test results, patients not receiving a proper change in mifepristone dose, by:

A) identification by the system of the combination of high starting dose with multiple refills, no scheduled appointments, no upcoming laboratory draws, and patient is elderly; or B) identification by the system of a low starting dose with multiple refills, and no scheduled appointments;

wherein said desired result comprises proper change in the patient's mifepristone dose level and one or more of improved patient compliance; improved treatment efficacy; improved patient outcome; improved adherence to a treatment regimen; improved adherence to a treatment regimen update; and improved adherence to a regimen modification;

determining a plurality of tasks for addressing the intervention,
wherein said intervention comprises modifying a patient's prescribed mifepristone dose, wherein said modification is selected from i) increasing said mifepristone dose when the system identifies that the physician has not increased the patient's dose to a level that will likely generate a therapeutic effect and ii) limiting the mifepristone dosage to avoid unfavorable side effects; and providing guidance relating to the treatment or determining whether follow-up blood work was planned, or both;
tasking the intervention by outputting an intervention alert or information communication to one or more different entities with the one or more electronic devices to facilitate the desired result; and
administering said modified mifepristone dose to the Cushing's syndrome patient.

2. The method of claim 1, wherein the tasks of the plurality of tasks are determined by the system to be performed according to i) a particular sequence, ii) particular timing, or both i) and ii).

3. The method of claim 2, wherein tasking the intervention comprises tasking the tasks of the plurality of tasks to different entities according to the particular sequence, timing, or according to both the particular sequence and timing.

4. The method of claim 1, wherein tasking the intervention comprises coordinating performance of the tasks by receiving information or a confirmation, or both, regarding a first task of the plurality before tasking a second task of the plurality of tasks.

5. The method of claim 1, wherein the intervention corresponds to a change in treatment determined by the system based on information received by the system in one or more tasks of the plurality of tasks.

6. The method of claim 1, wherein said intervention further requires a pharmacist to contact a physician to discuss any adverse events before the pharmacist fills a prescription for said glucocorticoid receptor antagonist.

7. The method of claim 1, wherein tasking the intervention comprises identifying an individual, position, or computer device to perform the intervention.

8. The method of claim 1, wherein the desired result is associated with any of patient compliance, treatment efficacy, patient outcome, a regulatory process, a business process, an administrative process, or any combination thereof.

9. The method of claim 1, wherein the one or more computerized devices receiving the intervention alert output comprise a phone, a mobile personal device, a user interface terminal or any combination thereof.

10. The method of claim 1, wherein the alert output comprises an electronic communication, indicator or combination thereof.

11. The method of claim 1, wherein the intervention comprises an automated task performed by the one or more computerized devices.

12. The method of claim 1, wherein the intervention alert is output to one or more computerized devices associated with the patient or a patient advocate.

13. The method of claim 1, wherein the intervention alert is output to one or more computerized devices associated with a treating physician, medical facility, medical administrator, insurer, or any combination thereof.

14. The method of claim 1, wherein outputting the intervention alert comprises identifying an intended recipient of the intervention alert and assigning a task to the intended recipient.

15. The method of claim 14, wherein the intended recipient is a pharmacist and the assigned task comprises contacting the patient's physician to i) assess the treatment regimen, ii) manage the treatment regimen, iii) update the treatment regimen, or combinations thereof.

16. The method of claim 14, wherein the intended recipient comprises a pharmaceutical manufacturer representative and the task comprises contacting the physician to discuss information relating to the drug protocol or treatment regimen.

17. The method of claim 14, wherein the intended recipient is a third-party associated with a program specific to the patient and the task comprises contacting the patient to discuss the treatment regimen, to manage the treatment regimen, or both.

18. The method of claim 14, wherein the intended recipient is an automated system and the task comprises generating a communication to the physician or patient relating to the treatment regimen.

19. A method of managing drug treatment of a Cushing's syndrome patient using an information system having a processor and a relational database, wherein the drug treatment comprises administration of mifepristone to said Cushing's syndrome patient, the method comprising:
Accessing, by said processor, a plurality of fields of information relating to said patient or treatment from a plurality of different information systems on which the plurality of fields of information are stored, wherein the plurality of fields of information comprises one or more of a patient identifier, patient characteristic, treatment regimen information, drug dose information, drug refill history, physician information, transaction date, symptom reporting, patient communication, and physician communication;
Relating, by the processor, the fields of information of the plurality using a relational database of the system and determining the need for an intervention based on the relationships of the fields of information of the plurality to facilitate a desired result,
Wherein identifying said need for an intervention comprises identifying, without requiring test results, patients not receiving a proper change in mifepristone dose, and is determined by:
A) identification by the system of the combination of high starting dose with multiple refills, no scheduled appointments, no upcoming laboratory draws, and patient is elderly; or
B) identification by the system of a low starting dose with multiple refills, and no scheduled appointments;
wherein said desired result comprises proper change in the patient's mifepristone dose level and one or more of improved patient compliance; improved treatment efficacy; improved patient outcome; improved adherence to a treatment regimen; improved adherence to a treatment regimen update; and improved adherence to a regimen modification;
determining, by the processor, a plurality of tasks associated with the intervention with the system
wherein said intervention comprises modifying a patient's prescribed mifepristone dose, wherein said modification is selected from i) increasing said mifepristone dose when the system identifies that the physician has not increased the patient's dose to a level that will likely generate a therapeutic effect and ii) limiting the mifepristone dosage to avoid unfavorable side effects; and providing guidance relating to the treatment or determining whether follow-up blood work was planned, or both;

performing, tasking, or both performing and tasking, by the processor, the plurality of tasks to multiple different entities according to a particular sequence and/or timing; and administering said modified mifepristone dose to the Cushing's syndrome patient.

* * * * *